United States Patent [19]

Kaiser

[11] 4,183,852
[45] Jan. 15, 1980

[54] PROCESS FOR PREPARING 25-HYDROXYCHOLESTEROL

[76] Inventor: Emil T. Kaiser, 5634 S. Woodlawn Ave., Chicago, Ill. 60637

[21] Appl. No.: 816,478

[22] Filed: Jul. 18, 1977

[51] Int. Cl.$^2$ .......................... C07J 17/00; C07J 9/00
[52] U.S. Cl. ...................... 260/239.55 R; 260/397.1; 260/397.5; 260/397.2
[58] Field of Search ................... 260/397.2, 239.55 R, 260/397.1, 397.5; /Steroids MS File

[56] References Cited

U.S. PATENT DOCUMENTS

| 3,257,384 | 6/1966 | Nelson | 260/239.5 |
| 3,833,622 | 9/1974 | Babcock et al. | 260/397.2 |

*Primary Examiner*—Alan L. Rotman
*Assistant Examiner*—Robert C. Whittenbaugh
*Attorney, Agent, or Firm*—Carl C. Batz

[57] ABSTRACT

The synthesis of 25-hydroxycholesterol and 25-hydroxycholecalciferol from animal bile starting materials in which hyodeoxycholic acid or an ester thereof is converted to the 3β-hydroxy-5-cholenic acid alkyl ester, and this is converted to 3β-hydroxy-25-cyano-5-cholene by a series of steps by which the sterol nucleus is stabilized by placing a protecting group at the 3 position and then extending the chain from the carbon at the 24 position to a cyanide group at the 25 position. The compound so formed is subjected to a series of reactions by which it is transformed into 25-hydroxy-7-dehydrocholesterol which may then be irradiated with ultraviolet light to 25-hydroxycholecalciferol. The invention discloses new and improved processes for preparing these end products and also new compounds formed as intermediates and processes for preparing these intermediates.

10 Claims, No Drawings

PROCESS FOR PREPARING 25-HYDROXYCHOLESTEROL

This invention relates to cholecalciferol derivatives having biological activity and to processes and compounds useful in the synthesis of such compounds and derivatives. More particularly this invention relates to the synthesis of 25-hydroxycholesterol and 25-hydroxycholecalciferol and to compounds and processes useful in the synthesis of these compounds.

BACKGROUND

Vitamin $D_3$, which is cholecalciferol, has been known for many years. It may be prepared from cholesterol by the introduction of an additional bond into the cholesterol molecule to produce 7-dehydrocholesterol and subjecting the 7-dehydrocholesterol to ultraviolet irradiation. It was at one time thought to be biologically active in the regulation of intestinal calcium transport and the mobilization of calcium from bone.

Recently, it has been discovered that to be biologically active the cholecalciferol has to be hydroxylated in the body to 25-hydroxycholecalciferol or certain derivatives thereof, and it is the 25-hydroxycholecalciferol and derivatives thereof which are active in regulating intestinal calcium transport and mobilization of calcium from bone. It would, therefore, be important to prepare and administer 25-hydroxycholecalciferol instead of Vitamin $D_3$.

It is known that 25-hydroxycholecalciferol can be produced by ultraviolet radiation of its provitamin 25-hydroxy-7-dehydro-cholesterol but it has not heretofore been possible to obtain 25-hydroxycholesterol except in amounts so small as to make it impractical for use in the preparation of 25-hydroxycholecalciferol. The transformation of 25-hydroxycholesterol to 25-hydroxy-7-dehydrocholesterol and the preparation of 25-hydroxycholecalciferol from the 7-dehydro compound by irradiation with ultraviolet light was described by J. W. Blunt and H. F. DeLuca in *Biochemistry* 8, 671 (1969). The biological activity of the synthetic 25-hydroxycholecalciferol was also assayed by the same authors, and the results published in their paper.

Sources from which 25-hydroxycholesterol has been prepared in small amounts include: cholesterol, stigmasterol $3\beta$-hydroxypregn-5-ene (synthesized from a natural source) and ergosterol (from which 25-hydroxy-7-dehydrocholesterol may be obtained). Yields in these syntheses are usually poor, chemicals needed for carrying out the procedures may have to be specially prepared, and in some cases special equipment is required which may not be conveniently available in a plant producing industrial chemicals.

The synthesis of 25-hydroxycholesterol by E. J. Semmler, M. F. Holic, H. K. Schnoes and H. F. DeLuca (Tetrahedron Letters, 4147 (1972)) begins with the oxidation of cholesterol. The oxidation product is converted to i-homocholanic acid methyl ether which is esterified with diazomethane, a dangerous, explosive compound. Then by a number of steps a hydroxyl group is introduced into position 6. Without counting the preparation of i-homocholanic acid, 18 steps are required to introduce the hydroxyl groups. Further, the scarcity of the starting material makes the method impractical for large scale manufacture.

Accordingly, I have set about to discover a new synthesis of 25-hydroxycholecalciferol, and particularly a new synthesis of 25-hydroxy-7-dehydrocholesterol. I have sought such a synthesis for which a starting material is readily available and in which high yields of 25-hydroxycholesterol or 25-hydroxycholecalciferol may be obtained. Further, I have sought syntheses in which the chemicals necessary for conducting the necessary reactions are commercially available and reasonably priced and I have sought such syntheses which utilize equipment generally available in chemical manufacturing plants so as to avoid the need for large capital investments.

SUMMARY

I have discovered that by using starting materials obtained from animal bile, it is possible to synthesize effectively and in relatively high yields the 25-hydroxycholesterol from which the desired 25-hydroxycholecalciferol may easily be obtained. This synthesis utilizes chemicals which are readily available and reasonably priced, and requires only such equipment as is commonly at hand in chemical manufacturing plants.

Animal bile, and particularly hog bile, is a by-product of slaughtering operations and is considered a waste material, there being at this time no industrial use for it. However, procedures are known for recovering from the bile hyodeoxycholic acid either as such or in the form of its methyl ester.

DISCLOSURE OF THE INVENTION

The synthesis may start with hyodeoxycholic acid which has been obtained from bile and which may be structually represented as:

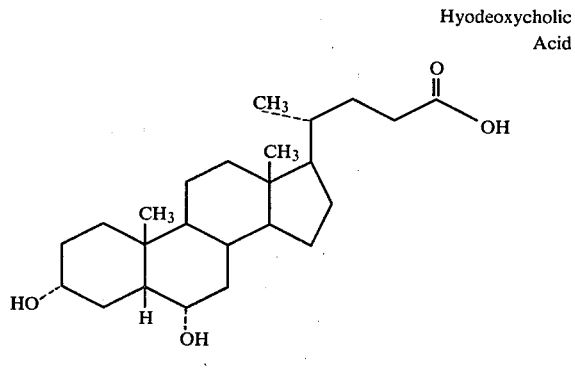

Hyodeoxycholic Acid

This may be reacted with any aliphatic alcohol to convert it to a carboxylic acid ester. Since the ester group is later removed to regenerate the free carboxylic acid group, the choice of the alcohol group is guided mainly by economic considerations and solubility properties of the ester. Any aliphatic, aromatic or cyclic alcohol could be used, but I prefer to form the methyl ester. It forms benzene complexes which facilitate isolation of the hyodeoxycholic acid methyl ester from hog bile. The alkyl ester may be written as:

Compound A

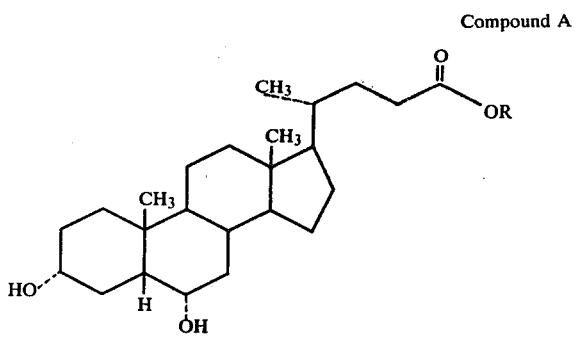

where R is an alkyl, aryl or cyclic group; or we may start with the methyl ester, Compound A, which has been obtained directly from bile. In either case the alkyl ester may be reacted with p-toluenesulfonyl halide and pyridine to obtain the hyodeoxycholic ester which has the structure:

Compound B

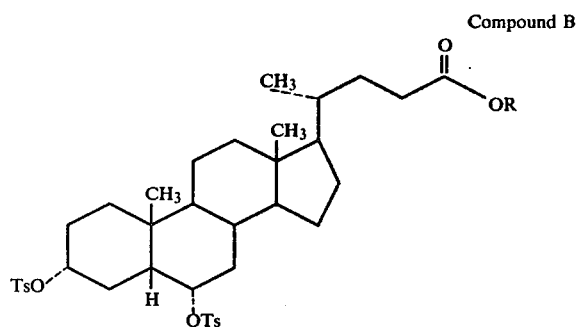

where R is an alkyl, aryl or cyclic group.

Compound B may be heated with KOAc and dimethylformamide-water, suitably at 105° C., for a period of several hours, suitably about 6 hours, to obtain 3β-acetoxy-5-cholenic acid ester which may be written as:

Compound C

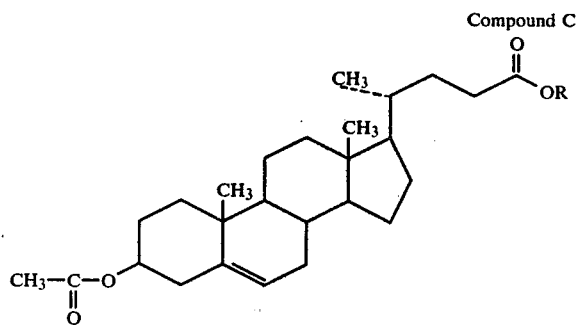

where R is an alkyl, aryl or cyclic group. The term "alkyl" as used in this application and unless otherwise specified includes the unsaturated or alkylene as well as the saturated form of this group.

Compound C may then be reacted with an alkali to remove R and the acetyl group and then acidified to obtain 3β-hydroxy-5-cholenic acid which has the structure:

Compound D

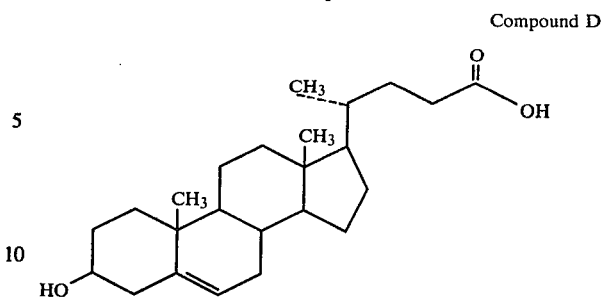

Compound D may simultaneously be esterified to obtain 3β-hydroxy-5-cholenic acid alkyl ester having the structure:

Compound E

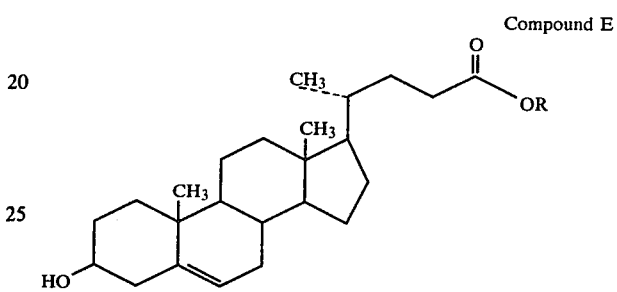

where R is alkyl, aryl or cyclic. Here too, the choice of R may be guided by economic considerations and by the solubility properties of the ester, since the ester group will be removed in reduction reactions which will later be described. The methyl or ethyl esters are the most accessible and economically advantageous of the Compound E esters.

Synthesis of the above compounds A to E according to the scheme above outlined, using methyl as the 24-alkyl group, is known to the art and is set forth in detail in an article by K. R. Barucha, G. C. Buckley, C. K. Cross, L. R. Rubin and P. Ziegler in Can. J. Chem., 34 982 (1956). Yields of Compound E according to this method have been found to be good and yields of over 50% of the starting material may be expected.

The next series of steps in the synthesis involves the placement of a protective group at the 3-position to stabilize the steroid nucleus during subsequent reactions involving alkaline reducing agents, preliminary to the extension of the side chain by one carbon. Such reagents may be lithium, potassium or sodium complexes of aluminum hydride which reduce the carboxylic ester groups to primary alcohols. As mentioned before, this reduction is not limited to any particular type of carboxylic acid ester. In *Organic Reactions,* Volume VI, John Wiley and Sons, Inc., New York (1951), Professor Weldon C. Brown describes in Chapter 10, starting on page 469, the scope and limitations of reductions by lithium aluminum hydride. On page 477, the reduction of esters is described without limitations on the scope of the reductions by the nature of the alcohol used to esterify the carboxyl group. The product of the reaction is a primary alcohol formed from the carboxyl group, and the esterifying alcohol is eliminated in this reaction. I prefer to esterify Compound D by refluxing it in methanol containing p-toluenesulfonic acid as a catalyst.

Ether derivatives of alcohols are found to be resistant to the proposed reducing agents. Any heterocyclic or alkyl group may be utilized in forming an ether for the protection of the 3-hydroxyl function. The heterocyclic or alkyl groups may be introduced by coupling the alkoxide form of the alcohol with the corresponding heterocyclic or alkyl halide. While not limiting the scope of this invention to any particular ether forming procedure, I prefer the method in which the 2-tetrahydropyranyl (THP) group, a heterocyclic group, is attached to the 3β-hydroxyl or the method in which the β-methoxyethoxymethyl (MEM) ether, an aliphatic ether, is formed. I find that the ease of ether formation and the mild conditions of the protecting group make these methods preferable to others. Mixing Compound E with dihydropyrane at an alkaline pH, suitably pH 8, attaches a THP protecting group to the 3-hydroxyl, or MEM protection can be introduced by mixing MEM halide with Compound E in the presence of diisopropyl ethylamine. The protected esters are 3β-(2-tetrahydropyranyloxy)-5-cholenic acid ester and the 3β-(β-methoxyethoxymethoxy)-5-cholenic acid ester. These esters are designated Compound F and have the structure:

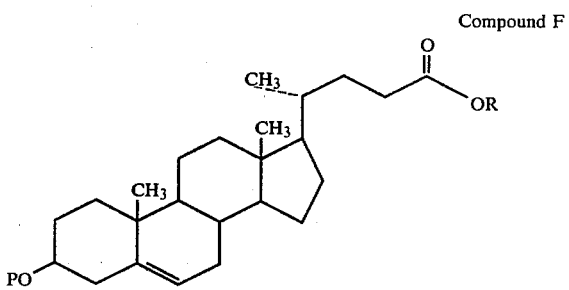

Compound F where P is heterocyclic or alkyl and R is an alkyl, aryl or cyclic group. For convenience, the Compound F having THP at the 3-position is designated Fa and the Compound F having MEM at the 3-position is designated Fb.

Although in the preparation of Compound F above described the protectant P as THP or MEM, it is understood that in this step and subsequent steps of the synthesis I may use as the protectant P any other heterocyclic or alkyl group.

Compound F can then be treated with a reducing agent to reduce the 24-carboxylic ester groups to a 24-hydroxyl group. The reducing agent as stated before may be a complex of aluminum hydride with sodium, potassium or lithium. This complex does not affect the now protected nucleus of Compound F. This reduction in one of its forms can be carried out in benzene solutions with sodium bis(2-methoxyethoxy) aluminum hydride (Vitride) or with lithium aluminum hydride by refluxing for a period sufficient to complete the reaction which may be, for example, about 1½ hours. The compound so obtained, with the preferred protecting groups 3β-(2-tetrahydropyranyloxy)-24-hydroxy-5-cholene or 3β-(β-methoxyethoxymethoxy)-24-hydroxy-4-cholene has the structure:

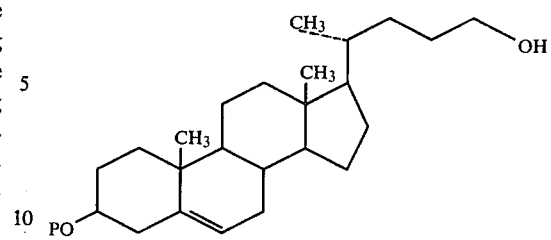

Compound G where P is 2-tetrahydropyranyl or β-methoxyethoxymethyl.

While the protecting group is still in position 3, Compound G may be mixed with p-toluenesulfonyl halide in pyridine solution and allowed to react to replace the hydroxyl with —OTs to obtain the Compound H which may be written:

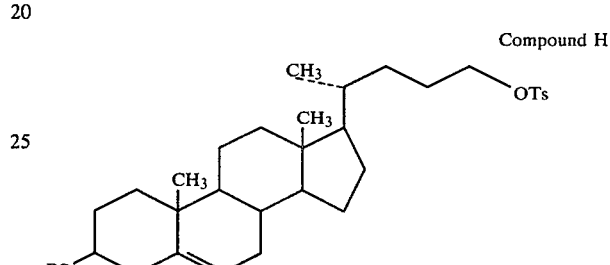

Compound H where P is 2-tetrahydropyranyl or β-methoxyethoxymethyl.

Optionally, and in place of the Ts group, Compound G can be mesylated with alkylsulfonyl halide such as methanesulfonyl halide to form a sulfonyl ester. Alternatively, by heating with alkali halide, the sulfonyl ester group of Compound H can be replaced by halogen, yielding a compound of the structure:

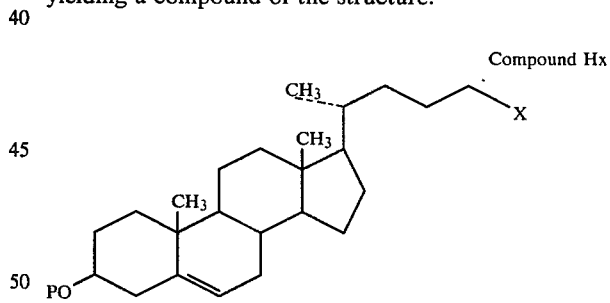

Compound Hx where X is chlorine, bromine or iodine. This alternate form of Compound H may, for convenience, be designated Hx.

In Compound H as first described above or in its alternate form Hx with a halogen in the side-chain, the steroid nucleus is still stabilized by the presence of the protecting group in the 3-position.

Compound H may be reacted with a metallic cyanide, preferably potassium cyanide, but other metallic cyanides, such as sodium cyanide, lithium cyanide, or silver cyanide may also be used to replace the side-chain of Compound H or the X-halogen group of the side-chain structure with CN. The crucially important extension of the side-chain by one carbon has now been accomplished, and a 25-carbon structure obtained with the carbon of the CN group being carbon 25.

In one of its forms the reaction between Compound H and potassium cyanide can be carried out by heating in dimethylformamide (DMF) for a period until the reaction is complete, for example, at about 98° C. for about 25 hours. Depending upon whether the preferred THP or MEM protecting group is used, the resulting compound is 3β-(2-tetrahydropyranyloxy)-25-cyano-5-cholene or 3β-(β-methoxyethoxymethoxy)-25-cyano-5-cholene which has the structure:

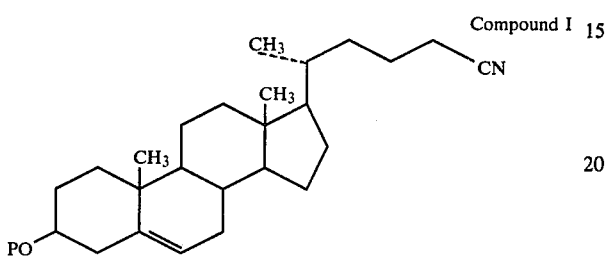

Compound I where P is tetrahydropyranyl or β-methoxyethoxymethyl.

Then the hydroxyl group may be restored by a mild acid hydrolysis when P is the THP group. This hydrolysis may be carried out by refluxing in aqueous ethanol with p-toluenesulfonic acid for a period until the reaction is complete, usually 4 hours or more. When P is the MEM group, a treatment with solid zinc bromide in methylene chloride will remove the MEM protection. A procedure using zinc bromide for deprotection of certain MEM ethers is described by E. J. Corey, J. L. Gras and P. Ulrich, *Tetrahedron Letters*, 809 (1976). In either case, the resulting compound is 3β-hydroxy-25-cyano-5-cholene having the structure:

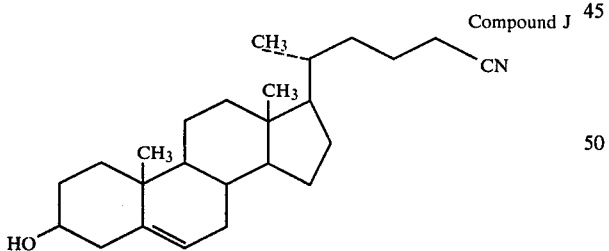

Compound J

In the next series of steps Compound J may be converted to the 3β-hydroxy-5-homo-cholenic acid methyl ester, as described by E. J. Semmler, M. F. Holic, H. K. Schnoes and H. P. DeLuca, *Tetrahedron Letters*, 4147 (1972).

Preferably, the cyano group of Compound J may be transformed into a carboxyl group by refluxing in ethanol solution with potassium hydroxide. By acidification, the free acid, 3β-hydroxy-5-homocholenic acid, is obtained, having the structure:

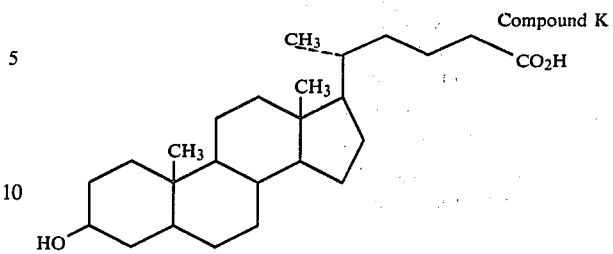

Compound K

A novelty in this step is that Compound K is obtained by saponification of a 25-cyano group. Compound K may then be refluxed in a methanol solution with p-toluenesulfonic acid as a catalyst to obtain 3β-hydroxy-5-homocholenic acid methyl ester, having the structure:

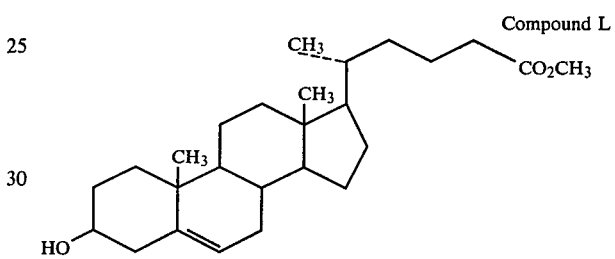

Compound L

Compound L may be mixed with a methyl magnesium Grignard reagent in tetrahydrofuran or a methyl lithium reagent and allowed to react to obtain 25-hydroxycholesterol having the structure:

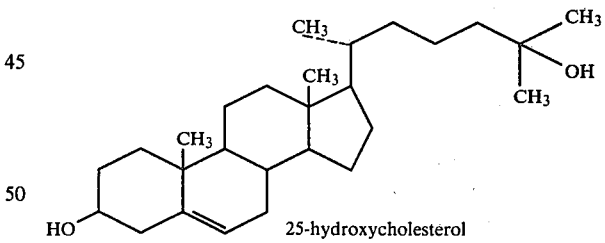

25-hydroxycholesterol

The transformation of 25-hydroxycholesterol to 25-hydroxy-7-dehydrocholesterol, and the irradiation of the latter compound with ultraviolet light to obtain synthetic 25-hydroxycholecalciferol is described by J. W. Blunt and H. F. DeLuca in *Biochemistry*, 8, 671 (1969). The biological activity of the synthetic 25-hydroxycholecalciferol, identical with that of the natural 25-hydroxycholecalciferol, is also reported in this paper.

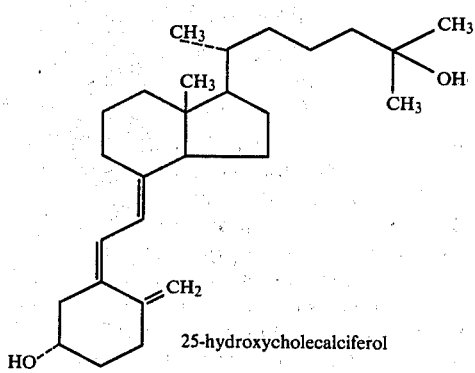

25-hydroxycholecalciferol

Special attention is called to the series of steps in which Compound E is converted to Compound J. In this transformation, a chemical group is added at position 3 which serves to stabilize the sterol nucleus while reactions take place to extend the side chain of the 24-carboxylic group, adding a carbon at the 25-position. Such transformation has been unknown to this art, and the procedures for accomplishing it, which are herein disclosed, have been found to be easily performed. Overall yields starting from hyodeoxycholic acid methyl ester in excess of 30% have been obtained.

To illustrate more specifically how the reaction may be practiced the following specific examples are set forth.

EXAMPLE 1

Converson of Hyodeoxycholic Acid Methyl Ester to 3β-Acetoxy-5-Cholenic Acid Methyl Ester Hog bile was saponified with alkali, the mixture acidified, and the precipitated acids esterified with methanol. Hyodeoxycholic acid methyl ester was separated from this ester mixture as a complex with benzene.

56.8 g (0.140 mole) of hyodeoxycholic acid methyl ester was dissolved in 295 ml of dry pyridine and 66.6 g of p-toluenesulfonyl chloride was added. After 48 hours in a refrigerator the mixture was poured into 600 ml of ice water and 600 ml of ice-cold concentrated hydrochloric acid was added. After stirring for ½ hour, the precipitate was collected on a filter, washed with water, and dried. 97.4 g of hyodeoxycholic acid methyl ester ditosylate was obtained, yield 97.4%, mp 155°–157° C. Anal. Calcd for $C_{39}H_{54}S_2O_8$: C, 65.52; H, 7.61; S, 8.97. Found: C, 65.12; H, 7.54; S, 8.60.

102.5 g of the hyodeoxycholic acid ditosylate and a solution of 49.7 g of potassium acetate in 72 ml of water were added to 820 ml of dimethylformamide, and the mixture was stirred and heated to 105° C. for six hours. It was cooled to room temperature and poured into 2.0 liters of ice-cold hydrochloric acid. The precipitate was collected on a filter, washed with water and dried. The crude 3β-acetoxy-5-cholenic acid methyl ester weighed 57 g. A sample crystallized from ethyl acetate had mp 158°–161° C. Anal. Calcd for $C_{27}H_{42}O_4$: C, 75.31; H, 9.43. Found: C, 75.94; H, 9.53.

60.1 g of the crude 3β-acetoxy-5-cholenic acid methyl ester was refluxed with a solution of 56.0 g of potassium hydroxide in 1.35 liters of methanol for two hours. The solution was cooled to room temperature and poured into 500 ml of 10% hydrochloric acid. The precipitate was isolated by filtration, washed with water and dried. The crude 3β-hydroxy-5-cholenic acid weighed 50.1 g. Of this, 20.3 g was refluxed for 22 hours with 2 liters of methanol containing 1 g of p-toluenesulfonic acid. The solvent was removed by distillation, the residue dissolved in ether, washed with dilute alkali and water, and the solvent evaporated. 20.3 g of 3β-hydroxy-5-cholenic acid methyl ester was obtained. On recrystallization from heptane the mp was 144°–145° C. Anal. Calcd for $C_{25}H_{40}O_3$: C, 77.27; H, 10.38. Found: C, 77.04; H, 10.01.

EXAMPLE 2

Preparation of 3β-(2-tetrahydropyranyloxy)-5-cholenic acid methyl ester (Compound F)

36.1 g (0.093 mole) of 3β-hydroxy-5-cholenic acid methyl ester was dissolved in 722 ml of dioxane at room temperature, and 1.81 g (0.05 mole of p-toluenesulfonic acid was added. Then, 26.83 ml (0.294 mole) of dihydropyrane was added dropwise over a period of 10 minutes. The temperature rose to 23°–27° C. The solution was stirred for two more hours at room temperature and then adjusted to pH 8 with 3.4 ml of a mixture of 1:1 methanol 29% ammonium hydroxide. An oily precipitate began forming. A semi-solid residue was obtained after the solvent was evaporated. The residue was dissolved in 1.1 liters of chloroform, washed with a 15% sodium bicarbonate solution, then with water. The chloroform solution was dried, decolorized with charcoal and evaporated. The solid residue was dissolved in 1.5 liters of boiling methanol, allowed to cool to room temperature and then filtered. The dried product weighed 34.5 g, mp 114°–115° C. (989-161-A). From the filtrate an additional amount of 8.0 g was isolated, which was recrystallized again from methanol and then from n-heptane. The second crop was 4.1 g, making a total of 38.6 g of 3β-(2-tetrahydropyranyloxy)-5-cholenic acid methyl ester, yield 84%. Anal. Calcd for $C_{30}H_{48}O_4$, M. W. 472.715: C, 76.22; H, 10.24; O, 13.54. Found: C, 76.37; H, 10.21; O, 13.28 (989-161-A). NMR (989-157-A) (CDCl₃): δ5.22–5.43 (m,1H, vinyl), 4.62–4.80 (m, 1H, 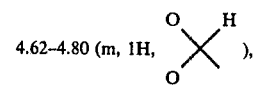 ), 3.20–4.10 (br m, 3H, adjacent to oxygen), 3.63 (s, 3H, —OCH₃), 1.00 (s, 3H, C-19 —CH₃), 0.66 (s, 3H, C-18 —CH₃). IR (989-157-A) (CHCl₃) 2940, 2860, 1730, 1440, 1170, 1135, 1110, 1075, 1030, 1020 cm⁻¹.

EXAMPLE 3

Preparation of 3β-(2-tetrahydropyranyloxy)-24-hydroxy-5-cholene (Compound G) with Vitride In 140 ml of benzene, 47.5 ml of Vitride (sodium bis (2-methoxyethoxy)aluminum hydride)), amounting to 0.1713 mole, was dissolved. The solution was heated to reflux and 36.8 g (0.7785 mole) of 3β-(2-tetrahydropyranyloxy)-5-cholenic acid methyl ester in 200 ml of benzene was added within 1½ hours. After one more hour of refluxing the reaction mixture was allowed to cool to room temperature with continuous stirring. Then, it was transferred into a separatory funnel, the flask was washed with 50 ml benzene and the mixture was added from the funnel to a stirred solution of 120 ml of 20% aq.sodium hydroxide. The temperature of the alkaline mixture was kept at about 19° C. with cooling. After the addition was completed, stirring was continued for one more hour. The two layers were allowed to separate, the aqueous layer extracted with 3×20 ml benzene and the combined benzene layers washed with water. The benzene solution was dried, decolorized with charcoal and evaporated. The white residue weighed 33.8 g and had mp 133°–135° C. (984-163-A). This was the 3β-(2-tetrahydropyranyloxy)-24-hydroxy-5-cholene, yield 98%. Anal. Calcd for $C_{29}H_{48}O_3$, M. W. 404.704: C, 78.33; H, 10.88; O, 10.79. Found: C, 78.88; H, 10.76; O, 11.10. NMR (989-163-A)(CDCl$_3$): δ5.22–5.43 (m, 1H, vinyl),

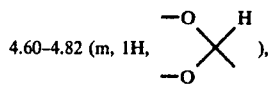

4.60–4.82 (m, 1H, 3.23–4.17 (br m, 5H, adjacent to oxygen), 1.00 (s, 3H, C-19 —CH$_3$), 0.66 (s, 3H, c-18 —CH$_3$). IR (989-163-A)(CHCl$_3$): 3620, 3450, 2945, 2870, 1470, 1455, 1445, 1380, 1140, 1115, 1080, 1060, 1025, 980 cm$^{-1}$.

EXAMPLE 4

Preparation of
3β-(2-tetrahydropyranyloxy)-24-hydroxy-5-cholene (Compound G) with lithium aluminum hydride This process was carried out in the same manner as described in Example 3 except that 0.1713 mole of lithium aluminum hydride was used instead of Vitride, and 3β-(2-tetrahydropyranyloxy)-24-hydroxy-5-cholene, mp 133°–135° C. was obtained.

EXAMPLE 5

Preparation of
3β-(2-tetrahydropyranyloxy)-24-(p-toluenesulfonoxy)-5-cholene (Compound H)

33.5 g (0.073 mole) of 3β-(2-tetrahydropyranyloxy)-24-hydroxy-5-cholene and 17.4 g (0.0913 mole) of p-toluenesulfonyl chloride were added to 125 ml of pyridine. The mixture was stored in a refrigerator for 40 hours. Then, it was poured into 475 ml of an ice-water mixture with stirring. The milky liquid was extracted with 1.8 liters of chloroform (slow separation), and the chloroform washed with water. After drying, the chloroform was evaporated. A viscous liquid residue was obtained, weighing 35.0 g (989-166-A), which solidified and had a melting point of 97°–104° C. By further extraction of the aqueous layer, 2.61 g more of the same substance was obtained. By NMR and IR spectroscopy this material was identified as the desired compound 3β-(2-tetrahydropyranyloxy)-24-(p-toluenesulfonoxy)-5-cholene. Yield, 78%. Anal. Calcd for $C_{36}H_{54}SO_5$, M. W. 598.893: C, 72.20; H, 9.09; S, 5.35; O, 13.36. Found: C, 72.29; H, 8.99; S, 5.12; O, 13.64. NMR (989-106-A)(CDCl$_3$): δ7.18–7.80 (AB$_q$, 4H, aromatic), 5.16–5.42 (m, 1H, vinyl),

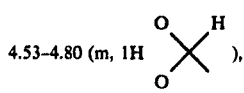

4.53–4.80 (m, 1H 3.16–4.16 (br m, 5H, adjacent to oxygen), 2.43 (s, 3H, —ArCH$_3$), 0.99 (s, 3H, C-19 —CH$_3$), 0.63 (s, 3H, C-18 —CH$_3$). IR (989-166-A)(CHCl$_3$) 2940, 2860, 1465, 1450, 1440, 1360, 1190, 1180, 1130, 1075, 1030, 1020, 970, 915 cm$^{-1}$.

EXAMPLE 6

Preparation of
3β-(2-tetrahydropyranyloxy)-25-cyano-5-cholene (Compound I)

A mixture of 27.7 g (0.0452 mole) of 3β-(2-tetrahydropyranyloxy)-24-(p-toluenesulfonoxy)-5-cholene, 17.7 g of powdered sodium cyanide and one liter of dimethylformamide were heated to 98° C. for 45 hours. After cooling to room temperature, the liquid was poured into 2.2 liters of an ice-water mixture and concentrated on a flash evaporator. To the residue 1.2 liters of water was added and extracted with 2 liters of chloroform. The chloroform layer was dried and concentrated to a dark brown liquid. To this, n-heptane was added and the mixture evaporated. 23.0 g of a brown solid was obtained, mp 132°–135° (989-179-A). This crude material was separated into fractions by crystallization from n-heptane, but all fractions yielded the same cyano compound. By NMR and IR spectroscopy the fractions were identified as the desired compounds, the 3β-(2-tetrahydropyranyloxy)-25-cyano-5-cholene, yield 97%. A sample crystallized from n-heptane had mp 143°–144° C. Anal. Calcd for $C_{30}H_{47}O_2N$, M.W. 435.715: C, 79.52; H, 10.44; N, 3.09; O, 7.05. Found: C, 79.12; H, 10.35; N, 3.21; O, 7.14. NMR (989-179-A-I)(CDCl$_3$): δ5.18–5.42 (m, 1H, vinyl),

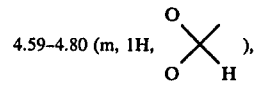

4.59–4.80 (m, 1H, 3.17–4.13 (br m, 3H, adjacent to oxygen), 2.10–2.50 (br t, 2H, adjacent to —CH), 1.00 (s, 3H, C-19 —CH$_3$), 0.66 (s, 3H, C-18 —CH$_3$). IR (989-179-A-I)(CHCl$_3$): 2950, 2870, 2250, 1470, 1460, 1445, 1380, 1140, 1120, 1080, 1060, 1035, 1030, 995, 980 cm$^{-1}$. Mass spectrum: m/e 388 (M+), 370, 277, 213.

EXAMPLE 7

Preparation of
3β-(2-tetrahydropyranyloxy)-25-cyano-5-cholene from 3β-(2-tetrahydropyranyloxy)-24-bromo-5-cholene 27.7 g (0.00452 mole) of 3β-(2-tetrahydropyranyloxy)-24-(p-toluenesulfonoxy)-5-cholene and 4.69 g (0.0452 mole) of sodium bromide were refluxed with 100 ml of acetone for 24 hours, then cooled and poured into water. The mixture was extracted with ethyl acetate, the organic layer washed with saturated sodium chloride solution and dried. The solvent was removed by evaporation and the residue, the 3β-(2-tetrahydropyranyloxy)-24-bromo-5-cholene, was heated with 100 ml of dimethylformamide and 1.8 g of powdered KCN to 98° C. for 45 hours. The mixture was worked up in the same manner as in Example 6, and 3β-(2-tetrahydropyranyloxy)-25-cyano-5-cholene was obtained.

EXAMPLE 8

Preparation of 3β-hydroxy-25-cyano-5-cholene (Compound J)

9.8 g (0.0216 mole) of 3β-(2-tetrahydropyranyloxy)-25-cyano-5-cholene and 0.98 g of p-toluenesulfonic acid were dissolved in a mixture of 360 ml ethanol and 112 ml water. The solution was heated at reflux for 4 hours and then the ethanol and water were evaporated. The residue was stirred with 250 ml of water, filtered, and washed on the filter with 200 ml of water. The solid was dried. It weighed 7.95 g (989-187-A) and was identified by IR and NMR spectroscopy as the desired 3β-hydroxy-25-cyano-5-cholene, mp 183°–186° C., yield 100%. Anal. Calcd for C$_{25}$H$_{39}$NO, M.W. 369.596: C, 81.24; H, 10.64; N, 3.79; O, 4.33. Found: C, 81.04; H, 10.67; N, 3.78; O, 4.16. Mass spectrum: m/e 369 (M+), 351, 336, 258.

EXAMPLE 9

Preparation of 3β-hydroxy-5-homocholenic acid (Compound K)

11.5 g of 3β-hydroxy-25-cyano-5-cholene, prepared according to Example 8, was added to a mixture of 160 ml ethanol and 160 ml 10 N sodium hydroxide solution. The mixture was refluxed for 72 hours and poured, while hot, into 800 ml water. While still warm, the pH was adjusted to pH 3 with 5% hydrochloric acid. After cooling to room temperature, the precipitate was removed by filtration, washed with water, and dried. 11.44 g of a solid was obtained, mp 213–214 (989-191-A). This was the desired compound, 3β-hydroxy-5-homocholenic acid, yield 98%.

A sample was recrystallized from an acetic acid-water mixture, mp 216–217. Anal. Calcd for C$_{25}$H$_{40}$O$_3$, M.W. 300.279: C, 77.27; H, 10.38; O, 12.35. Found: C, 76.92; H, 10.35; O, 12.50. IR (989-191-A) (Nujol): 3390, 1725 cm$^{-1}$. Mass spectrum: m/e 388 (M+), 370, 277, 213.

EXAMPLE 10

Preparation of 3β-hydroxy-5-homocholenic acid methyl ester 11.12 g (0.0286 mole) of 3β-hydroxy-5-homocholenic acid, prepared according to Example 8, and 0.56 g of p-toluenesulfonic acid (5% of the steroid's weight) were stirred and refluxed in 1.1 liter anhydrous methanol for 48 hours. Before returning the condensed methanol vapors to the reaction vessel, they were passed through the thimble of a Soxhlet apparatus which was filled with molecular sieves. The water formed in the esterification process was continuously removed in this manner. After the addition of charcoal, the methanol solution was filtered and evaporated. The dried residue was stirred with 280 ml of hot n-heptane and filtered through a pre-heated filter. On filtration 0.4 g remained undissolved, containing mainly p-toluenesulfonic acid. On cooling, 9.43 g of a white solid was obtained from the filtrate. This was the desired compound, 3β-hydroxy-5-homocholenic acid methyl ester, yield 82%, mp 112°–114° C. The structure was confirmed by NMR and IR data and also by carbon and hydrogen analysis. Anal. Calcd. for C$_{26}$H$_{42}$O$_3$, M.W. 402.623: C, 77.57; H, 10.51; O, 11.92. Found: C, 77.38; H, 10.31; O, 11.87. NMR (989-194-A-I)(CDCl$_3$): δ5.20–5.40 (m 1H, vinyl), 3.65 (s, 3H, OCH$_3$),

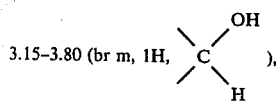

2.16 (s, 1H—OH), 1.00 (s, 3H, C-19 —CH$_3$), 0.68 (s, 3H, C-18—CH$_3$). IR (989-194-A-I): 3615, 3460, 2950, 2875, 1730, 1465, 1440, 1380, 1175, 1045, 1020 cm$^{-1}$. Mass spectrum: m/e 402 (M+), 384, 355, 291, 145.

EXAMPLE 11

Preparation of 25-hydroxycholesterol 0.506 g (0.00126 mole) of 3β-hydroxy-5-homocholenic acid methyl ester was heated with 20 ml tetrahydrofuran for 20 minutes. This slightly cloudy solution was added to a mixture of 55 ml tetrahydrofuran and 6.2 ml (0.01132 mole) of a 1.84 M solution of methyllithium in ether over a period of 10 minutes, at room temperature and under a flow of argon. Stirring at room temperature was continued for 24 hours under a flow of argon. The gel-like reaction mixture was poured into 17 ml of cold water, containing 2.5 g of ammonium chloride. After stirring for one hour, the mixture was evaporated to dryness. To the residue, 50 ml of water and 700 ml of ether were added, stirred, and the ether solution separated. After drying, the solvent was evaporated. The residue weighed 0.583 g, mp 168°–175° (cloudy)(989-197-A).

Of this crude material 0.571 g was dissolved in 40 ml of methanol, heated with charcoal, filtered, and the filtrate concentrated to 10 ml. This was cooled to room temperature, filtered and washed with methanol. The mother liquor was further concentrated, and a second crop of solid obtained.

The first crop, weighing 0.34 g, shrank at 170° C., melted at 174°–177° (cloudy); it cleared up at 260° upon rapid heating (989-197-A-I).

The second crop, 0.159 g, was dissolved in 17 ml of boiling heptane, cooled to 10° and the solution was filtered. The solid material isolated weighed 0.118 g, mp 173°–177° (989-197-B-I).

IR and NMR data identified the first crop and the recrystallized second crop also as 25-hydroxycholesterol. Total yield: 93% of 25-hydroxycholesterol. NMR (989-152-A-I)(CDCl$_3$) δ5.20–5.40 (m, 1H, vinyl),

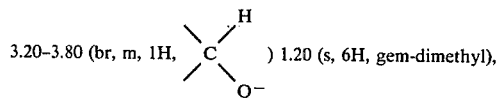

1.00 (s, 3H, C-19 —CH$_3$), 0.67 (s, 3H, C-18 —CH$_3$).

Carbon, hydrogen, and oxygen determinations were carried out on the sample obtained in this Example 11, in which methyl magnesium bromide was used.

EXAMPLE 12

Preparation of 25-hydroxycholesterol

To 40 ml of tetrahydrofuran, 4.2 ml (0.0122 mole) of a 2.92 M solution of methyl magnesium bromide in ether was added under a stream of argon. With stirring and under a continued stream of argon, a solution of 0.544 g (0.00135 mole) of 3β-hydroxy-5-homocholenic acid methyl ester in 20 ml of THF was added dropwise. The reaction mixture was stirred at room temperature for 24 hours under an argon atmosphere, then poured into a cooled solution of 2.6 g ammonium chloride in 19 ml water. The transfer of the reaction mixture was completed by rinsing with 50 ml tetrahydrofuran. Cooling and stirring was continued for one more hour. The mixture was concentrated in vacuo until a wet slurry remained. To this, 60 ml of water and 400 ml ether were added. The water insoluble material dissolved in ether, which was separated, dried and evaporated. The residue weighed 0.6 g, melted at 172°–177° C. (cloudy), and started boiling on rapid heating to 230° (989-189-A).

0.59 g of the crude product was dissolved in 40 ml of boiling n-heptanol, cooled to 10° and filtered. The first crop of solid obtained weighed 0.51 g (989-198-A-I). From the filtrate a second crop, 0.082 g, was obtained.

The melting point of the first crop was 175°-178° C. (clear liquid). It was identified as 25-hydroxycholesterol, yield 96%. Literature mp 175°-177° C. For twice recrystallized, mp 178°-180° (Helv., 57, 770 (1974)). Anal. Calcd. for $C_{27}H_{46}O_2$, M.W. 402.667: C, 80.54; H, 11.51; O, 7.95. Found: C, 80.47; H, 11.38; O, 7.91. Mass spectrum: m/e 402 (M+), 384, 369, 351, 299, 273, 271, 255, 231, 213, 185, 173, 171, 161, 159, 158, 149, 147, 145, 143, 135, 133, 131, 123, 121, 120, 119, 117, 111, 109, 107, 105, 100, 97, 95, 93, 91, 85, 83, 81, 79, 71, 69, 67, 59 (base peak), 55, 44, 43, 41. IR (989-154-A-II)(CHCl$_3$): 3620, 3460, 2960, 2890, 1475, 1318, 1140, 1060, 1030, 965, 915 cm$^{-1}$.

EXAMPLE 13

Preparation of 3β-(methoxyethoxymethoxy)-5-cholenic acid methyl ester

A 100 ml round bottom flask, equipped with a mercury relief valve and magnetic stirrer, was flame-dried and flushed with nitrogen. The flask was charged with 2.57 mmoles (1.0 g) of 3β-hydroxy-5-cholenic acid methyl ester, 3.86 mmoles (0.50 g) of diisopropylethylamine, 3.86 mmoles (0.48 g) of methoxyethoxymethyl chloride and 10 ml of CH$_2$Cl$_2$. The reaction mixture was stirred for 48 hours at room temperature. After stirring, the reaction mixture was diluted with 25 ml of pentane, washed with 20 ml of 10% acetic acid and 20 ml of saturated sodium bicarbonate. The combined aqueous layers were extracted with two twenty ml portions of ether and the organic layers separated and dried with MgSO$_4$. Concentration of the ether solution left an oily crude product (96%) which was isolated as a pure white solid (84%) by dissolving the oil in pentane, cooling to −78° C., and filtering. The pure solid had mp 44°-46° C.

EXAMPLE 14

Preparation of 3β-hydroxy-5-homocholenic acid from 3β-(methoxyethoxymethoxy)-5-cholenic acid methyl ester The 3β-(methoxyethoxymethoxy)-5-cholenic acid methyl ester was reduced with Vitride as described for the tetrahydropyranyl ether in Example 3. The resulting compound, the 3β-(methoxyethoxymethoxy)-24-hydroxy-5-cholene, was treated with tosyl chloride in pyridine and the 3β-(methoxyethoxymethoxy)-24-tosyloxy-5-cholene obtained. The tosyloxy compound was heated in dimethylformamide with potassium cyanide, and the tosyloxy group exchanged for the cyano group. 2.1 mmole of the 3β-(methoxyethoxymethoxy)-25-cyano-5-cholene was stirred with 2.36 g (10.5 mmole) of zinc bromide in 15 ml of methylene chloride. The insoluble material was removed by filtration, washed with ether, and the combined filtrates extracted with saturated aqueous solutions of sodium bicarbonate and sodium chloride. After drying, the solvents were evaporated, and the residue sponified with alkali. The 3β-hydroxy-5-homocholenic acid was obtained from the acidified saponification mixture.

While only certain embodiments and certain variations of my invention have been described it will be apparent to those skilled in this art that other embodiments may be practiced, and that many changes may be made all within the spirit of the invention, and all such embodiments and changes are considered to be embraced and included within the scope of the appended claims.

What is claimed is:

1. A steroid compound having the structure

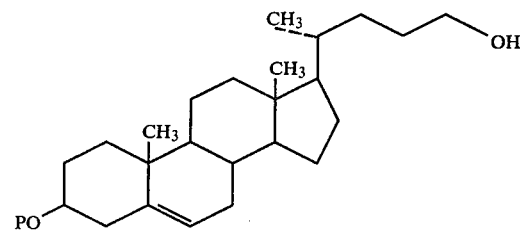

in which P is β-methoxyethoxymethyl.

2. A steroid compound having the structure

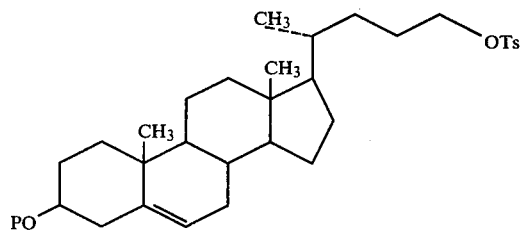

in which P is β-methoxyethoxymethyl and Ts is p-toluenesulfonyl.

3. A steroid compound having the structure

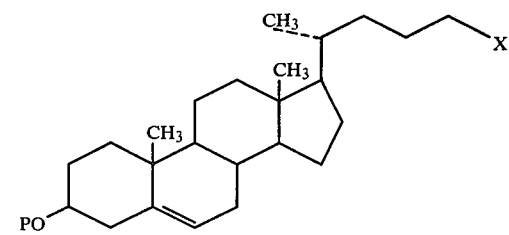

where X is chlorine, bromine or iodine and P is β-methoxyethoxymethyl.

4. A steroid compound having the structure

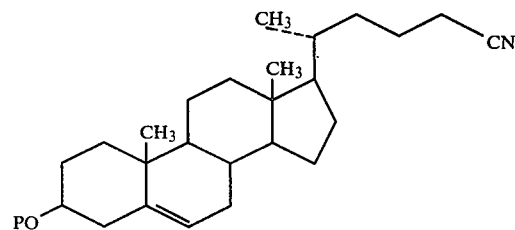

where P is 2-tetrahydropyranyl or β-methoxyethoxymethyl.

5. A steroid compound as set forth in claim 4 in which P is 2-tetrahydropyranyl.

6. A steroid compound as set forth in claim 4 in which P is β-methoxyethoxymethyl.

7. A steroid compound having the structure

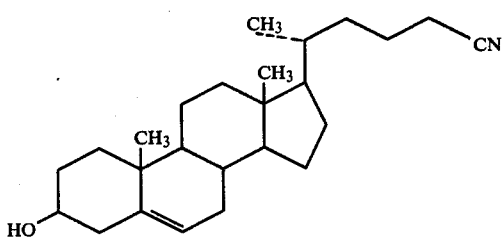

8. In a process for preparing 25-hydroxycholesterol, the step of refluxing

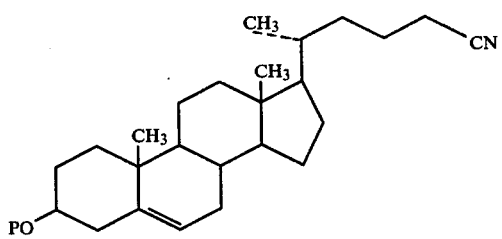

in aqueous alcohol with p-toluenesulfonic acid for a period until the reaction is complete to prepare

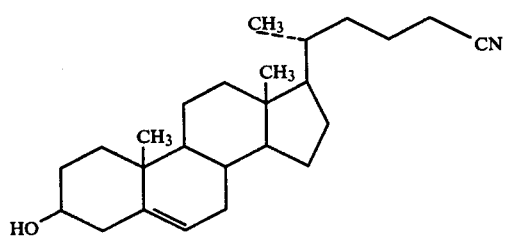

where P is tetrahydropyranyl.

9. In a process for preparing 25-hydroxycholesterol, the step of mixing

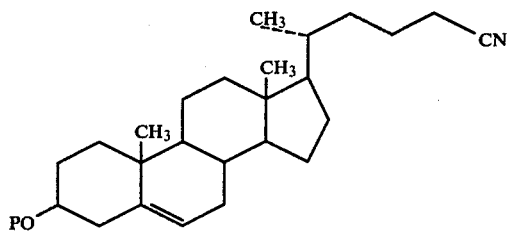

where P is β-methoxyethoxymethyl, with solid zinc bromide in methylene chloride to remove the β-methoxyethoxymethyl group.

10. In a process for preparing a sterol compound, the step of heating with a metal cyanide

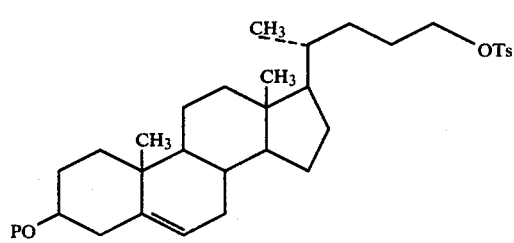

where P is a heterocyclic group having the pyran nucleus or a lower alkyl group or the β-methoxyethoxymethyl group and Ts is the p-toluenesulfonyl group, in dimethyformamide to prepare the compound

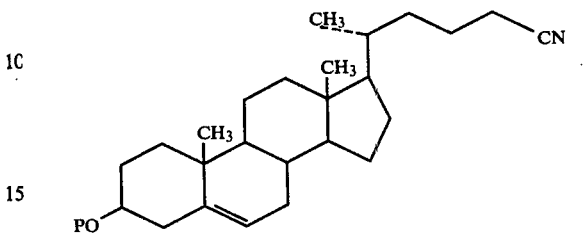

11. In a process for preparing 25-hydroxycholesterol, the step of refluxing

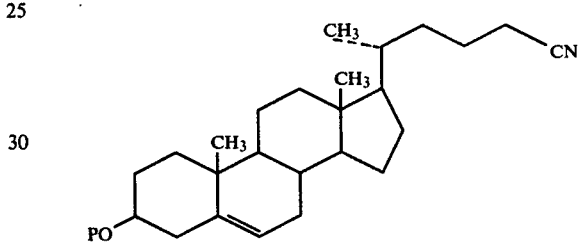

in aqueous alcohol with p-toluenesulfonic acid for a period until the reaction is complete to prepare

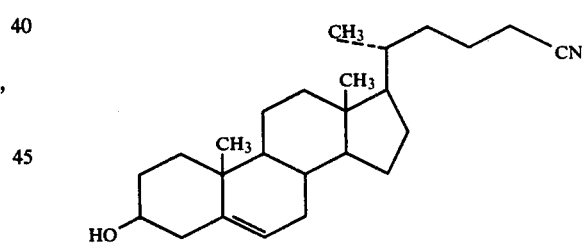

where P is tetrahydropyranyl.

12. In a process for preparing 25-hydroxycholesterol, the step of mixing

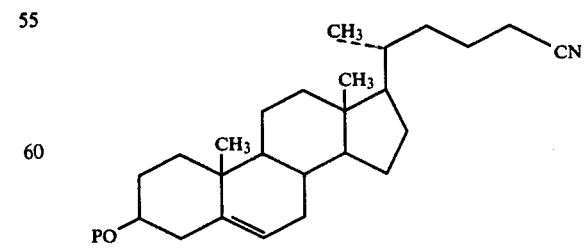

where P is β-amethoxyethoxymethyl, with solid zinc bromide in methylene chloride to remove the β-methoxyethoxymethyl group.

* * * * *